(12) United States Patent
Gardner, Jr. et al.

(10) Patent No.: US 8,320,637 B2
(45) Date of Patent: Nov. 27, 2012

(54) SYSTEM AND METHOD FOR HYPERSPECTRAL IMAGING OF TREATED FINGERPRINTS

(75) Inventors: Charles W. Gardner, Jr., Gibsonia, PA (US); David Exline, Gibsonia, PA (US); Sara Nedley, Allison Park, PA (US)

(73) Assignee: ChemImage Corporation, Pittsburgh, PA (US)

( * ) Notice: Subject to any disclaimer, the term of this patent is extended or adjusted under 35 U.S.C. 154(b) by 296 days.

(21) Appl. No.: 12/850,202

(22) Filed: Aug. 4, 2010

(65) Prior Publication Data

US 2011/0188714 A1    Aug. 4, 2011

Related U.S. Application Data

(60) Provisional application No. 61/231,077, filed on Aug. 4, 2009.

(51) Int. Cl.
*G06K 9/00* (2006.01)
*G01J 3/44* (2006.01)

(52) U.S. Cl. .................... 382/112; 382/274; 356/301

(58) Field of Classification Search ............ 382/100, 382/108, 112–116, 123–124, 128, 135–140, 382/154, 162, 168, 173, 181, 219, 232, 254, 382/274, 276, 305, 312; 356/419, 301, 237.4; 427/1; 250/288
See application file for complete search history.

(56) References Cited

U.S. PATENT DOCUMENTS

| 4,191,940 | A | * | 3/1980 | Polcyn et al. ............... 382/128 |
| 5,072,338 | A | | 12/1991 | Hug |
| 5,324,567 | A | | 6/1994 | Bratchley |
| 5,689,333 | A | | 11/1997 | Batchelder |
| 5,751,415 | A | | 5/1998 | Smith |
| 5,770,856 | A | | 6/1998 | Fillard |
| 6,002,476 | A | | 12/1999 | Treado |
| 6,008,888 | A | | 12/1999 | Nottke |
| 6,030,655 | A | * | 2/2000 | Hansmire et al. ............. 427/1 |
| 6,124,926 | A | * | 9/2000 | Ogawa et al. ............ 356/237.4 |
| 6,239,904 | B1 | | 5/2001 | Serfling |

(Continued)

FOREIGN PATENT DOCUMENTS

DE    4031753    4/1992

(Continued)

OTHER PUBLICATIONS

Azoury, M.G. (2003). ESDA Processing and Laten Fingerprint Development: The Humidity Effect. Journal of Forensic Sciences, 48 (3), 564-580.

(Continued)

*Primary Examiner* — Seyed Azarian

(57) ABSTRACT

The present disclosure provides for a method for analyzing treated fingerprints on a document. A sample document is provided. A digital image of the sample document is obtained. The sample document is treated with a reagent and a hyperspectral image of the document is obtained. The hyperspectral image of the document is analyzed to determine a region of interest and a hyperspectal image is obtained of the region of interest. The present disclosure also provides for a system comprising a carrier frame, an imaging station for obtaining a digital image of the sample document, a first processing station for treating the document and a second processing station for developing the treated document, a second imaging station for obtaining a hyperspectral image of at least one of the document and a region of interest of the document, and a robotic subsystem for transporting the document through the system.

29 Claims, 6 Drawing Sheets

Digital Image of Sample

Chemical Image at 610nm after only flat-field correction

U.S. PATENT DOCUMENTS

| | | | |
|---|---|---|---|
| 6,485,981 | B1 | 11/2002 | Fernandez |
| 6,552,794 | B2 | 4/2003 | Garini |
| 6,734,962 | B2 | 5/2004 | Treado |
| 6,774,950 | B1 | 8/2004 | Jiang |
| 6,822,228 | B2 * | 11/2004 | Scott et al. ............... 250/288 |
| 7,420,675 | B2 | 9/2008 | Giakos |
| 7,420,679 | B2 * | 9/2008 | Treado et al. ............... 356/419 |
| 7,869,031 | B2 * | 1/2011 | Lewis et al. ............... 356/301 |
| 2002/0065468 | A1 | 5/2002 | Utzinger |
| 2004/0114224 | A1 | 6/2004 | Rigler |
| 2005/0264813 | A1 | 12/2005 | Giakos |
| 2006/0126168 | A1 | 6/2006 | Treado |

FOREIGN PATENT DOCUMENTS

| | | |
|---|---|---|
| WO | WO96/37797 | 11/1996 |

OTHER PUBLICATIONS

Champond, C.L. (2004). Fingerprints and Other Ridge Skin Impression. Chapter 3. Boca Raton: CRC Press LLC.

Edwards, C.H. (1966). Some Observations on the Detection of Fingerprints using Ninhydri. Journal of the Forensic Science Society, 6(4), 183-184.

Exline, D.L. (2003). Forensic Applications of Chemical Imaging: Latent Fingerprint Detection Using Visible Absorption and Luminscence. Journal of Forensic Science, 48 (5), 1047-1053.

Hewlett, D.S. (1999). An Operational Trial of Two Non-ozone Depleting Ninhydrin Formulations for Laten Fingerprint Detection. Journal of Forensic Identification, 49(4), 388-396.

Lee, H.C. (2001), Advances in Fingerprint Technology. Chapters 4,5, and 8. Boca Raton: CRC Press LLC.

Payne, G. (2005). A Further Study to Investigate the Detection and Enhancement of Latent Fingerprints Using Visible absorption and Luminescence Chemical Imaging. Forensic Science International, 150(1), 33-51.

Rajtar, P.E. (n.d.), 3M™ Engineered Fluid HFE-7100. Retrieved Jul. 17, 2009. from 3M United States: http://multimedia.3M.com/mws/mediawebserver?66666UuZjcFSLXTtlxTcM8TEEVuQEcuZgVs6EVs6E666666~.

Conti, S. et al., Traces of Polymethylsilozane in Case Histories of Rape. Technique for Detection, Elsevier Science Ireland LTD, Forensic Science International, Jan. 1995, pp. 121-128.

Lee, G.S.H., et al, A Methodology Based on NMR Spectroscopy for the Forensic Analysis of Condoms, St. Andrews Centre for Advanced Materials, pp. 808-821.

Maynard, P. et al., A Protocol for the Forensic Analysis of Condom and Personal Lubricants Found in Sexual Assault Cases, Forensic Science International, 124(2001), pp. 140-156.

Stoilovic, M. et al., The Application of Light in Forensic Science & A Modern Approach to Fingerprint Detection and Enhancement, Australian Federal Police, AFP Workshop Manual, Oct. 2000.

Roux. C. et al. Evaluation of 1,2-indanedione and 5,6-Dimethoxy-1,2-Indanedione for the Detection of Latent Fingerprints on Porous Surfaces, Journal of Forensic Science, vol. 45(4) 2000. pp. 761-769.

Roux. C et al., A Study to Investigate the Evidential Value of Blue and Black Ballpoint Pen inks in Australia, Forensic Science International, 101 (1999) pp. 167-176.

Mazzella, W.D. et al., Classification and Identification of Photocopying Toners by Diffuse Reflectance Infrared Fourier Transform Spectroscopy (DRIFTS): I. Preliminary Results, Journal of Forensic Sciences, JFSCA, vol. 36, No. 2, Mar. 1991, pp. 449-465.

Bourelle, R.L., Questioned Document Examination. Bureau of Alcohol, Tobacco, and Firearms, U.S. Treasury Department, 1982.

Robertson, J. et al, The Persistence of Textile Fibres Transferred During Simulated Contacts. Journal of Forensic Sciences, vol. 22, No. 4. Oct. 1982, p. 353-360.

Gaudette,B.D., The Forensic Aspects of Textile Fiber Examination, Central Forensic Laboratory, Royal Canadian Mounted Police.

Pounds, C.A. et al., The Transfer of Fibres Between Clothing Materials During Simulated Contacts and their Persistence During Wear: Part I—fibre Persistence, Journal of Forensic Sciences, vol. 15, 1975 pp. 17-27.

Pounds, C.A. et al, The Transfer of Fibres Between Clothing Materials During Simulated Contacts and their Persistence During Wear; Part II—Fibre Persistence, Journal of Forensic Sciences, vol. 15, 1975 pp. 29-37.

Maynard, P. et al., Adhesive Tape Analysis: Establishing the Evidential Value of Specific Techniques, Journal of Forensic Sciences, vol. 46(2), 2001, pp. 280-287.

Foster+Freeman Brochure, Advanced Technology for Police and Forensic Science.

Renishaw PLC, Raman Spectroscopy Solutions for Forensic Science.

Tahtouh, Mark et al, "The Detection and Enhancement of Latent Fingerprints Using Infrared Chemical imaging," J. Forensic. Sci. Jan 2005. vol. 50, No. 1.

Tahtouh, Mark et al, The Application of Infrared Chemical Imaging to the Detection and Enhancement of Latent Fingerprints: Method Optimization and Further Findings, J. Forensic Sci. Sep. 2007, vol. 52, No. 5.

Champond. C.L. (2004). Fingerprints and Other Ridge Skin Impressions. Chapter 4 Boca Raton: CRC Press LLC.

* cited by examiner

Figure 4C
Chemical Image of Sample at 610nm after additional processing steps: Reconstruction of PCA frames, Euclidean Distance Analysis and Noise Reduction Filtering
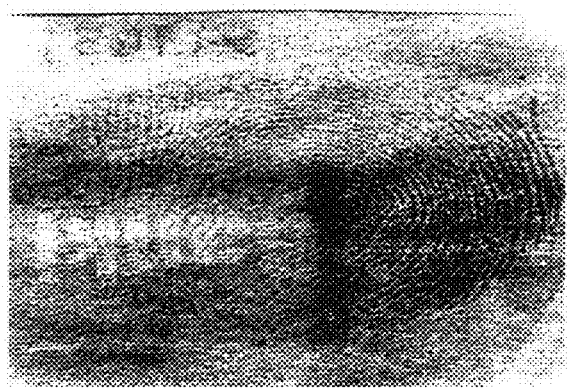
Figure 4B
Chemical Image at 610nm after only flat-field correction
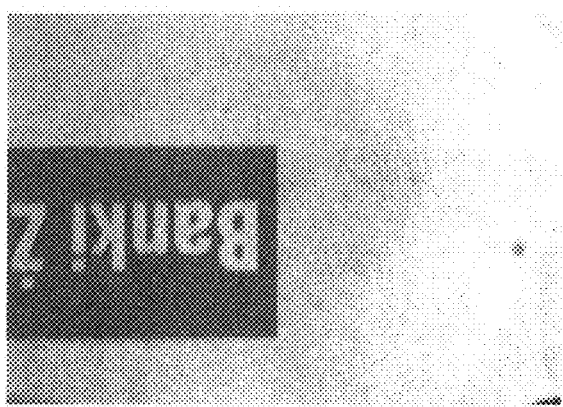
Figure 4A
Digital Image of Sample
Figure 4

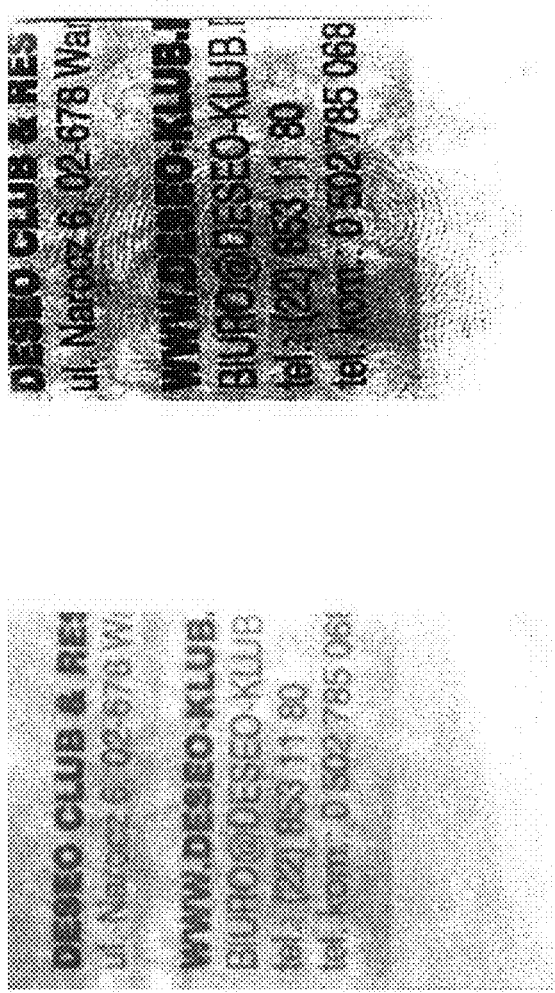
Figure 5C
Chemical Image of Sample at 590nm after additional processing steps: Reconstruction of PCA frames, Noise Reduction Filtering
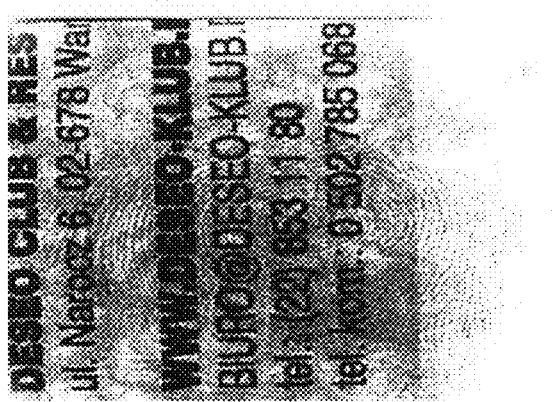
Figure 5B
Chemical Image at 590nm after only flat-field correction
Figure 5A
Digital Image of Sample
Figure 5

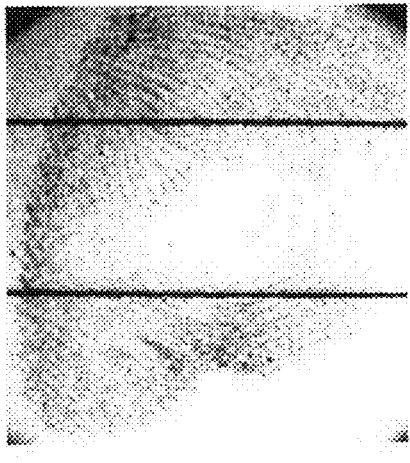
Figure 6C
Chemical Image of Sample after additional processing steps: Normalization, PCA, Reconstruction, Concatenation
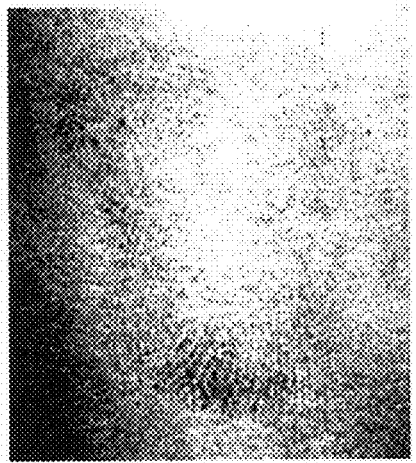
Figure 6B
Chemical Image at 430 nm after only flat-field correction
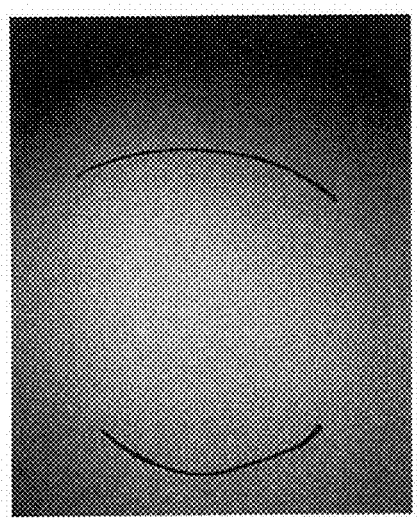
Figure 6A
Digital image of Sample
Figure 6

SYSTEM AND METHOD FOR HYPERSPECTRAL IMAGING OF TREATED FINGERPRINTS

RELATED APPLICATIONS

This application claims priority under 35 U.S.C. §119(e) to U.S. Provisional Patent Application No. 61/231,077, filed on Aug. 4, 2009, entitled "Systems and Methods for Improved Forensic Analysis", which is hereby incorporated by reference in its entirety.

BACKGROUND

Forensic analysis involves the observation and identification of an object that may exist in part or in its entirety on some sort of supporting surface. This analysis typically compares the sample in question to other possible reference samples or reference data to make an association that relates it to a specific person, place or event. Forensic analysis is widely used in law enforcement or legal disputes as evidence in a range of situations from homicide to fraud. More specifically, the goal is usually to provide evidence of the existence of a direct link, for example, between a suspect and a crime scene, a victim and a suspect, a weapon and a suspect, etc. To do so with a high degree of specificity and discrimination from possible variations of the sample is essential. Examples of forensic samples include, but are not limited to, fingerprints, gunshot residues, condom lubricants, multi-layer paint chips, fibers, ink samples and thin layer chromatography plates.

The quality of a forensic analysis is critical in making the association of evidence as unambiguous as possible, thereby providing compelling identifications and linkages. In many cases, such as with fingerprints, this identification has widely accepted requirements where as in others, such as fiber characterization and comparison, the uniqueness of the results can be disputed. Even the most unique and definitive identification of biological evidence based on genetic information has been successfully questioned and removed as compelling evidence. Minimizing the subjective components or features of a forensic analysis to make compelling identifications and linkages therefore becomes a critical aspect of all forensic analysis. Doing so quickly and in a cost effective manner is equally important.

In most legal cases, the ability of a jury or judge to understand the forensic evidence, and the ability of the scientist to convey its value determines the utility of the forensic method. As a result, methods which allow the objects to be visually compared or which show simple representations of the item under scrutiny are the most widely accepted and understood by non-specialists. Despite the existence of many advanced scientific techniques and analysis methods that are very sophisticated, many such techniques may not be understood by non-specialists, and may thereby raise some doubts as to its validity. Visual forensic analysis and visual comparisons are amongst the most widely accepted forensic methods used to date.

Advances in science and technology have enabled many new approaches to sample analysis, bringing forensic science into an era which goes far beyond the classic perception of an investigator looking thru a magnifying glass for small traces of evidence. Numerous techniques exist that allow detailed chemical and elemental identification. This includes most all analytical chemistry methods, such as mass spectroscopy, x-ray analysis, scanning electron microscopy and chromatography, that are widely used today to characterize gaseous, liquid and solid materials. Many of these methods are extremely sensitive and require finite material for their use that is consumed as part of the analysis process. Advances in the sensitivity of analytical chemistry methods and instruments over the years have reduced this problem but these methods are still not considered non-destructive. This becomes increasingly important as smaller and smaller pieces of pieces of evidence are examined and required in forensic analysis.

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, spectra can be collected over the an entire area encompassing the sample simultaneously using an electronically tunable optical imaging filter such as an acousto-optic tunable filter (AOTF) or a liquid crystal tunable filter ("LCTF"). Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

Currently there exists a need for accurately analyzing documents for latent fingerprints. There exists a need for a system and method to analyze a number of documents, detect latent fingerprints, and associate these latent fingerprints with an individual.

SUMMARY OF INVENTION

The present disclosure relates to the field of forensic analysis. The present disclosure provides for a system and method for multi-view digital imaging of forensic samples at multiple reflected, scattered, emitted, or absorbed wavelengths to provide new, detailed information to distinguish and differentiate forensic materials and samples. More specifically, the present disclosure provides for a system and method for analyzing fingerprints on documents using hyperspectral imaging. The system and method disclosed herein overcome the limitations of the prior art and allow for more subtle forensic features to be observed and related to the image of the sample or to known reference samples.

The system and method provided herein are based on three technologies: visualization of latent prints on documents using ninhydrin; enhancement of the visualization of ninhydrin processed prints through the use of hyperspectral imaging; and the use of laboratory robots (also referred to herein as a "robotic subsystem") to automate the transport of a "sample" through various automated processing and imaging stations.

The present disclosure provides for automatically taking a document loaded by an operator and, 1) collecting its color digital image, 2) performing ninhydrin processing on it, 3) collecting a widefield hyperspectral image set, 4) analyzing this image set to determine the location of possible latent prints, and 5) collecting a close-up hyperspectral image set from each of the possible prints. The disclosure may further provide for the steps of: 6) producing an IAFIS compatible image from the confirmed latent prints and 7) providing the necessary database functions to allow association of any observed latent print images, the close up hyperspectral image sets and the widefield hyperspectral image set with the original color digital image of the document and ultimately with the origin of the document.

The present disclosure provides for a system and method for the automated capture of latent prints. The present disclosure holds potential, for a variety of applications, including military applications. One field that may benefit from the system and method disclosed herein is battlefield forensics. In such an embodiment, the system first collects a "parent" (original document) image. The documents are then automatically transported to a chemical treatment module where a visualization reagent is applied, allowed to develop in a controlled humidity environment, and transported to the hyperspectral imager for collection of chemical imaging data sets. The requirement to produce both parent and child latent print images is addressed through the use of an automated zoom lens, the ability to precisely move the imaging system in the X and Y directions and an autonomous targeting system that identifies the position of a likely latent print directs the imaging system to take a chemical image at a higher spatial resolution at that location. Traceability is ensured in the information that is archived by the system about each sample.

Large quantities of documents exist related to military operations that must be evaluated to determine threat level. Manpower requirements to sort, chemically treat, process and visualize hundreds to thousands of documents are often not practical. The development and implementation of the system and method disclosed herein hold potential for relieving this burden and allowing forces to focus on probative information. This efficiency will not only expedite military operation and decision making, but will provide the military with state of the art fingerprint development technology and archival capability. Data basing of captured "child" fingerprints associated with "parent" documents will also provide a means for correlating documents in the future. Also, the use of an automated system that incorporates development technology in addition to visualization and storage will provide a safe and controlled environment for documents, regardless of the environment the system is working in. For instance, documents will be processed in the same conditions regardless of location, thus reducing subjectivity by different technical experts.

In one embodiment, ninhydrin can be used in conjunction with the systems and methods described herein. Use of nihydrin also holds potential for minimal document damage, optimum reaction with latent prints and in the development of environmentally and workplace-friendly formulations.

Hyperspectral imaging (HSI) technology (also known as chemical imaging) is the basis of the data collection, processing and visualization of the fingerprints in the system and method of the present disclosure. In reflectance HSI the document is illuminated with white light. The incident light interacts with the sample document and some of the light is reflected back off the surface. This reflected light is collected by a lens and sent to a tunable liquid crystal filter device which is set to allow light at one specific wavelength to reach a high-sensitivity CCD camera. This single-wavelength reflectance image is collected and stored and the filter is then tuned to another wavelength and the process repeated. This process continues over a predetermined wavelength range at a predetermined spectral step size to create a stack of images, taken at different wavelengths but all from the same region of the sample. This is the chemical image set (also known as the hyperspectral data cube), a 3-dimensional data structure having the spatial dimensions of X and Y as two axes, with a Z axis of wavelength.

If one makes a plot of the intensity of reflected light for any single pixel in the image set versus wavelength, a reflectance spectrum of that pixel is obtained. Extending this concept to the full XY region of the sample, it can be seen that chemical imaging produces a spectrum for each area of the sample captured by a single camera pixel. By creating this spectral and spatial information simultaneously, chemical imaging allows for easy subtraction of background materials and the various colors typical of documents. Do to the spectral uniqueness of each pixel within the image, additional spectral processing methods allow for isolating unique features such as fingerprints on backgrounds with significant texture and variable colors.

In current methods of fingerprint development, ninhydrin treated prints are often represented photographically as visualized following treatment. Hyperspectral imaging datasets provide spectral data for each individual pixel within the image, allowing increased contrast with colors that have only minimal colorimetric differences. The closely related colors, thus increasing contrast of a ninhydrin developed print on pink, purple, or red substrates with greater contrast than conventional visualization methods.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

FIGS. 4A, 4B, and 4C are illustrative of a ninhydrin treated fingerprint on newspaper with a colored background. FIG. 4A illustrates a digital image of a sample. FIG. 4B is illustrative of a chemical image of a sample at 610 nm after flat field correction. FIG. 4C is illustrative of a chemical image of a sample at 610 nm after additional processing steps: reconstruction of PCA frames Euclidean distance analysis, and noise reduction.

FIGS. 5A, 5B, and 5C are illustrative of a ninhydrin treated fingerprint on newspaper. FIG. 5A is illustrative of a digital image of a sample. FIG. 5B is illustrative of a chemical image of a sample at 590 nm after flat field correction. FIG. 5C is illustrative of a chemical image of a sample at 590 nm after additional processing steps: reconstruction of PCA frames and noise reduction filtering.

FIGS. 6A, 6B, and 6C are illustrative of latent prints as detected on untreated white paper. FIG. 6A is illustrative of a digital image of a sample. FIG. 6B is illustrative of a chemical image of a sample at 430 nm after flat field correction. FIG. 6C is illustrative of a chemical image of a sample after additional processing steps: normalization, PCA, reconstruction, and concatenation.

DETAILED DESCRIPTION

Reference will now be made in detail to the embodiments of the present disclosure, examples of which are illustrated in the accompanying drawings. Wherever possible, the same reference numbers will be used throughout the drawings to refer to the same or like parts.

Figure 1:
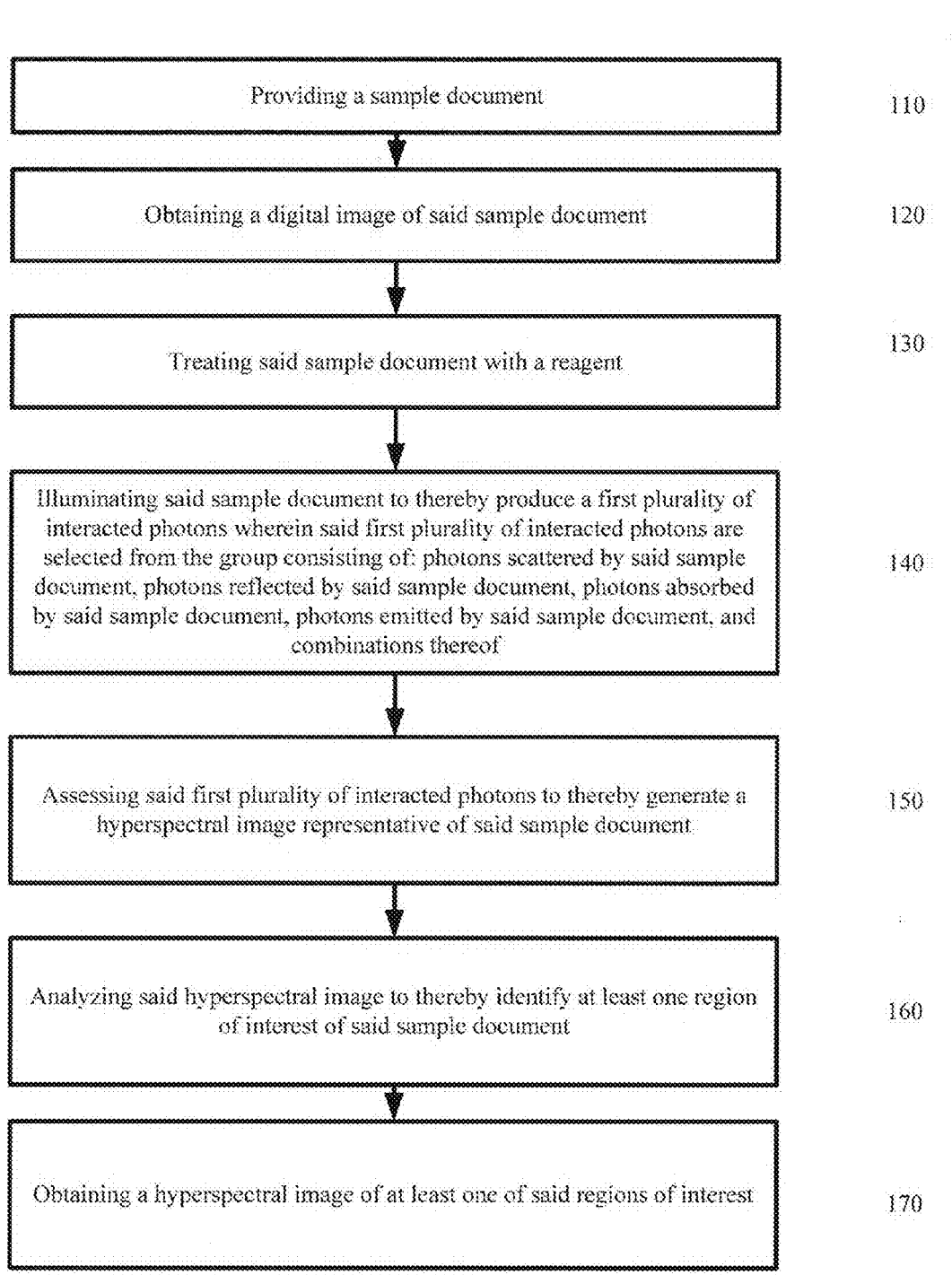
FIG. 1 is illustrative of a method of the present disclosure.

FIG. 1 illustrates a method of the present disclosure. The method 100 provides for providing a sample document in step 110. In step 120 a digital image is obtained of said sample document. In one embodiment, the digital image may comprise at least one of: a color digital image, a black and white digital image, a gray scale digital image, and combinations thereof. The sample document is treated with a reagent in step 130. In one embodiment, this reagent may comprise ninhydrin. In another embodiment, DFO, indian dione, or another suitable reagent known in the art may be used. In step 140 the sample document is illuminated to thereby generate a first plurality of interacted photons wherein said first plurality of interacted photons are selected from the group consisting of: photons scattered by said sample document, photons reflected by said sample document, photons absorbed by said sample document, photons emitted by said sample document, and combinations thereof. The first plurality of interacted photons are assessed in step 150 to thereby generate a hyperspectral image representative of said sample document. The hyperspectral image is analyzed in step 160 to thereby identify at least one region of interest of said sample document. In one embodiment, these regions of interest may be identified based on the color intensity of the location after reaction with the reagent. It is assumed that areas with fingerprints will react with the reagent to produce a color change on the sample document. Therefore, areas with high color intensity can be identified as areas with a high probability of comprising fingerprints. A hyperspectral image of at least one of said regions of interest is obtained in step 170.

In one embodiment, the method 100 may further comprise passing said first plurality of interacted photons through a tunable filter. The tunable filter may receive said first plurality of interacted photons and provide wavelength-selective filtered photons. In one embodiment, this tunable filter may be selected from the group consisting of: a multi-conjugate tunable filter, a liquid crystal tunable filter, acousto-optical tunable filters, Lyot liquid crystal tunable filter, Evans Split-Element liquid crystal tunable filter, Solc liquid crystal tunable filter, Ferroelectric liquid crystal tunable filter, Fabry Perot liquid crystal tunable filter, and combinations thereof. In one embodiment, the tunable filter may comprise multi-conjugate filter technology available from ChemImage Corporation, Pittsburgh, Pa. This technology is more fully described in U.S. Pat. No. 6,992,809, filed on Feb. 2, 2005, entitled "Multi-Conjugate Liquid Crystal Tunable Filter and U.S. Pat. No. 7,362,489, filed on Apr. 22, 2005, also entitled "Multi-Conjugate Liquid Crystal Tunable Filter." These patents are hereby incorporated by reference in their entireties. Potential benefits of using an MCF are more fully described in U.S. patent application Ser. No. 12/765,188, filed on May 24, 2010, entitled "System and Method for Improved Forensic Analysis", which is hereby incorporated by reference in its entirety.

The hyperspectral image representative of at least one of said document and said area of interest in said document may comprise an image and a fully resolved spectrum unique to the material for each pixel location in the image. In one embodiment, the hyperspectral image representative of at least one of said document and said area of interest may comprise a visible hyperspectral image.

In one embodiment, the method 100 may further comprise assigning an identifying mark to at least one of said document, said digital image representative of said document, said hyperspectral image representative of said document, said hyperspectral image representative of said region of interest of said document, and combinations thereof. In one embodiment, this identifying mark may comprise a barcode. In another embodiment, this identifying mark may be used as a means for associating one or more of the following: said document, said digital image representative of said document, said hyperspectral image representative of said document, said hyperspectral image representative of said region of interest of said document, and combinations thereof. Other means for associating said images may include image titles and serial numbers.

In one embodiment, the method 100 may further comprise comparing a detected fingerprint or portion of a detected fingerprint with one or more reference fingerprints present in a reference data base. In one embodiment, this may be accomplished by selecting points of interest on the fingerprint of the sample document and comparing these points of interest to a reference fingerprint. This comparison may be achieved using a chemometric technique known in the art, including but not limited to principle components analysis, partial least squares discriminate analysis, cosine correlation analysis, Euclidian distance analysis, k-means clustering, multivariate curve resolution, band t. entropy method, mahalanobis distance, adaptive subspace detector, spectral mixture resolution, and combinations thereof.

Based on this comparison, a determination can be made as to whether or not a match between the detected fingerprint of the sample document and the reference fingerprint has been made. If a match is found, then the detected fingerprint on the sample document can be attributed to the individual associated with the reference fingerprint. Therefore, the present disclosure provides a means for identifying individuals who have had contact with the sample document by analysis of latent fingerprints.

Figure 2:
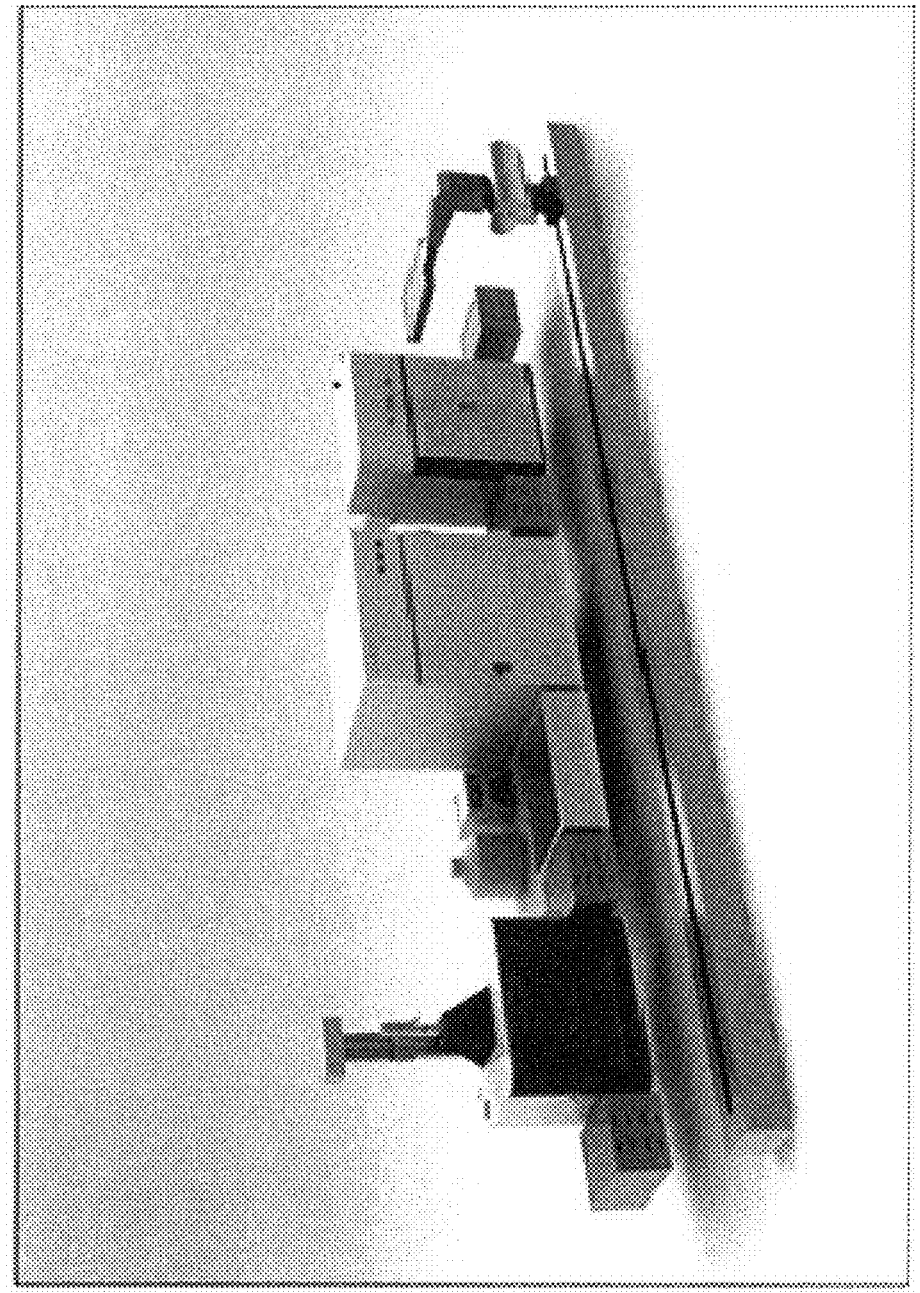
FIG. 2 is a schematic representation of exemplary packaging options of the system of the present disclosure.
Figure 3:
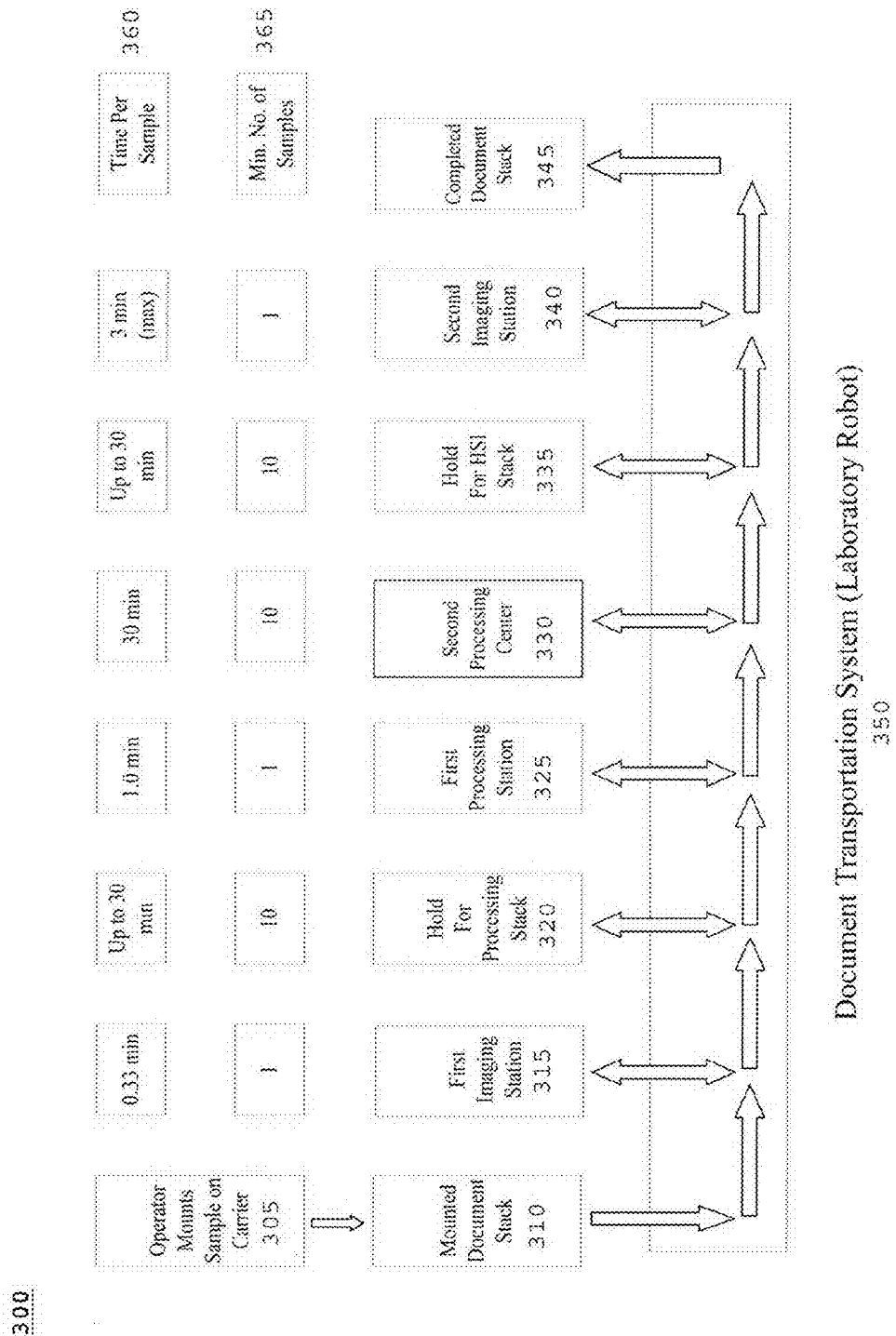
FIG. 3 is a schematic representation of one embodiment of a system of the present disclosure.

The present disclosure also provides for a system for analyzing treated fingerprints on documents. FIG. 2 is a schematic representation of an exemplary packaging option of a system of the present disclosure. FIG. 3 is a schematic representation of one embodiment of the overall system. FIG. 3 illustrates the system 300 as a collection of individual processing and imaging stations (elements 315, 325, 330, and 340), with sample accumulation stacks when necessary due to the time to execute each step (elements 310, 320, 335, and 345).

In one embodiment, the system 300 may achieve automation through a series of automated stations, each performing one key system function, with sample transport to each station performed by a robotic subsystem (laboratory robot system) 350 running in front of the individual stations as shown schematically in FIG. 3. FIG. 3 illustrates the overall system schematic of one embodiment of the present disclosure. Also illustrated in FIG. 3 are exemplary estimates of time per station 360 and maximum number of samples that can be handled simultaneously at the station 365. These configurations, are provided to illustrate potential operation of the system and method disclosed herein. However, it is noted that the system and method of the present disclosure are not limited to these configurations.

In one embodiment, the system and method of the present disclosure may be operated through a central computer system (not pictured). This computer may house a sample image data base and a reference image data base, provide scheduling and tracking information while a sample is being processed and imaged and may be in communication with the single-board computers that control and monitor each station. This distributed computing approach holds potential for allowing data intensive operations like the HSI widefield and close up imaging to take place locally at the second imaging station 340 and have no effect on the overall system operation. The system computer and each of the station computers may communicate though Ethernet network protocols.

In one embodiment of the present disclosure, all documents being examined, regardless of size, may be mounted on a carrier frame similar to a window screen. This is depicted in FIG. 3 as element 305. This frame may be designed to be picked up, transported, loaded into a station, removed from a station and stacked by a robot arm. In order to facilitate a number of stations placed side by side, the arm may be mounted on a moveable track 350, allowing the arm to be positioned in front of each station. Use of a robot-based sample transport element holds potential for easily adapting to new or additional processing stations.

In one embodiment, an operator may mount the sample document to be examined onto a specially designed carrier to facilitate document handling throughout the process 305. This carrier may be similar to a window screen. In one embodiment, the carrier may be configured to accommodate a variety of document sizes, including but not limited to 11×14 in. In one embodiment, the document being examined may be placed in one corner of the frame and held in place by a clip system designed for minimal obstruction of the document. However, the present disclosure contemplates that any mounting configuration that minimally obstructs the document so as to not interfere with processing and imaging may be used. It is assumed that many of the documents will be sensitive to handling, therefore this configuration may be advantageous over the use of highly automated paper feeders. The carrier approach allows for single handling of the document and holds potential for stabilizing the sample throughout the imaging, processing and relocation of developed fingerprint process. Each carrier may have a unique identification number, title and/or a bar code which will be associated with each examined document and each child image. The sample document may then be placed on the mounted document stack 310 until transported to the First Imaging Station 315.

The robot moves to the Mounted Document Stack 310 and picks up the top carrier, moves to the First Imaging Station 315 and inserts the document. In this station, a high resolution image of the entire document (the parent image) is taken and stored. In one embodiment this may comprise a digital image. In one embodiment, a barcode reader in the First Imaging Station 315 may read the ID of the carrier in order to make sure that the digital image gets associated with the correct document. Because the order in which the robot picks up the documents off the Mounted Document Stack may be random, verifying the identity of the document at this station will place the document identity in the system operation queue and will eliminate the need for ID verification at subsequent stations. After the image is collected, the robot removes the document from the First. Imaging Station 315 and places it on the Hold for Processing Stack 320.

The sample carrier containing the mounted document will transport the document into a First Processing Station 325 where it will undergo chemical processing. In one embodiment, this chemical processing may comprise treating the sample document with a reagent such as ninhydrin, a non-specific amino acid reagent. Having both stability and an affinity for cellulose, amino acids do not migrate through paper/porous items and therefore latent fingerprints can be rendered visible on such items through exposure to ninhydrin even years after the initial deposit of print residues. Ninhydrin is easy to mix, the chemicals are readily available, if stored properly the working and stock solutions can be used for up to a year, and although developed prints can be visualized without further aid prints of faint or partial development can be further enhanced by the use of HSI (560-580 nm). Due to these reasons, ninhydrin holds potential as an effective means of developing latent prints on paper surfaces.

Ninhydrin solutions consist of the reagent, a polar solvent to keep the reagent in solution, acetic acid and a carrier solvent that makes up the bulk of the solution. A ninhydrin solution of approximately 0.5% weight per volume in concentration is required for the development of fingerprints. An ideal carrier solution is volatile (evaporates readily as it delivers the reagent), nontoxic, nonflammable, and nonpolar (reduces ink bleeding on documents).

However, the present disclosure is not limited to the use of ninhydrin and contemplates that any reagent known in the art that is compatible with the system and method of the present disclosure may be used.

In one embodiment, the entire sample document may be treated with ninhydrin. This holds potential or optimizing the overall reaction. In one embodiment, treating the sample document may be accomplished by dipping the entire sample document in the solution. In such an embodiment, the sample document is submerged within the solution allowing the solvent to deliver the reagent to all areas of the surface. Dipping, also reduces the need to expose other areas of the developing chamber of the system to the ninhydrin solution. Other embodiments may utilize spraying and painting as methods for applying ninhydrin solutions.

To treat the sample document, the robot may load the document carrier into the First Processing Station 325. In the First Processing Station 325, a motorized rack is used to slowly dip the document and carrier into a tray containing the ninhydrin solution. The station may be enclosed and if necessary, it can be kept under a slight negative air pressure to allow for venting of the solvent vapor without causing gross solvent evaporation. The ninhydrin solution may be contained in a separate reservoir and a level sensor controlling a peristaltic pump may be used to keep the optimum level of ninhydrin solution in the dipping tray.

Once the document has been fully immersed in the solution, it may be raised back up and allowed to drip dry. The robot may then remove the carrier from the First Processing Station 325 and place it into the Second Processing Station 330 to develop Although ninhydrin readily reacts with amino acids, the reaction is not rapid. Ideally, documents processed with ninhydrin are allowed to fully develop over a period of 24-48 hours in a dark area, at ambient temperature and 50-80% relative humidity. Unfortunately, allowing documents one to two days to develop is not practical for the system and method disclosed herein, so accelerated development techniques will be employed. Environmental conditions, such as elevated temperature and controlled humidity, can be used to increase the development of latent prints treated with ninhydrin. Commercial systems are available that expose ninhydrin treated prints to humidity (60-70% RH) and heat (up to 80° C.). This holds potential for greatly reducing the development time. It is very important to precisely control acceleration conditions, as overheating items to accelerate development can lead to background coloration due to a reaction between ninhydrin and the substrate itself.

After the First Processing Station 325, the robot will load the carrier into a custom rack located in the Second Processing Station 330. Loading may occur in a precisely defined manner under the control of the system computer, so that sample traceability is preserved. Because it is anticipated that the longest step in the process may be the development of the ninhydrin stain, a plurality of sample documents may be developed simultaneously. This will increase the overall throughput.

The Second Processing Center 330 may be vented to remove any solvent vapors and will have the optional water recirculation station in order to minimize operator maintenance.

After the sample document is allowed to develop, the robotic subsystem 350 may transport the treated document to the Second Imaging Station 340. In one embodiment, the Second Imaging Station 340 may be configured to generate a hyperspectral image of the sample under analysis. In one embodiment, the Second Imaging Station 340 may be based on the CONDOR macroscopic chemical imaging Platform available from ChemImage Corporation, Pittsburgh, Pa. In one embodiment, the entire treated document is first subjected to widefield HSI to detect regions of interest wherein these regions of interest comprise potential "child" fingerprints. An analysis of the widefield image may produce coordinates for regions of interest that contain potential developed latent fingerprints. In one embodiment, these regions of interest can be identified by locating areas of the sample document with a high reaction to reagent (high color intensity). In one embodiment, this may comprise locating areas with high color contrast in certain areas with respect to the rest of the sample document. These areas may then be identified as areas with a high probability of comprising at least a portion of a fingerprint.

These coordinates may be stored with the "parent" image data file. A set of single wavelength, high resolution images may be taken from each area of interest and stamped with XY coordinates relative to the "parent" image. The area of interest datasets may be processed using optimized software visualization tools and stored with the parent data. In one embodiment, this software may comprise ChemImage Xpert software, available from ChemImage Corporation, Pittsburgh, Pa.

In one embodiment, this software may be adapted to identify regions of the sample document that have increased contrast after ninhydrin treatment and flag their XY coordinates for close up imaging. The hyperspectral imaging optics, lens, filter and camera may be mounted on an XY gantry which allows the imager subsystem to center itself on each of these XY coordinates and take a close up image. An automated zoom lens allows for computer control of the magnification and thus the image resolution.

In one embodiment, a HSI camera with greater than a 2000×2000 pixel format may be used in the Second Imaging Station 330 to comply with the 1000 line per inch image requirement for IAFIS compatibility. This will allow the production of close up images, approximately 1.5 in.×1.5 in. and at a spatial resolution greater than the IAFIS standard. This software will be applied to the conversion of the collected close up images for use in IAFIS. Following chemical imaging analysis at the Second Imaging Station 330, the robot may remove the document from the Station and place it on the Completed Document Stack 345. In one embodiment, the operator may remove the carrier from the system at this point and remove the document from the carrier and archive the document for further examinations. Until the document is removed from the carrier, the carrier ID may be used for sample tracking. In one embodiment, once the document is removed from the carrier, the operator may "log" the sample out of the system, which may release the carrier to be cleaned and reused on another sample document.

In one embodiment, the present disclosure contemplates a system wherein the digital image and the hyperspectral images are obtained at the same imaging station.

The use of chemical imaging in this system is advantageous over other systems of the prior art that use common digital representation of developed fingerprints. Chemical imaging produces a spectrum for each area of the sample captured in a single camera pixel. By creating this spectral and spatial information simultaneously, chemical imaging allows for easy subtraction of background materials and the various colors typical of documents. Due to the spectral uniqueness of each pixel within the image, additional spectral processing methods allow for isolating unique features such as fingerprints on backgrounds with significant texture and variable colors. This is imperative in this type of evaluation when samples of different colored backgrounds are certain. An example of resulting chemical images on such difficult backgrounds is shown in FIG. 4. FIG. 4A illustrates a digital image of a sample. FIG. 4B is illustrative of a chemical image of a sample at 610 nm after flat field correction. FIG. 4C is illustrative of a chemical image of a sample at 610 nm after additional processing steps: reconstruction of PCA frames, Euclidean distance analysis, and noise reduction. As can be seen from FIGS. 4A, 4B, and 4C, chemical imaging holds potential for increasing visualization of ninhydrin treated fingerprints on newspaper with a color background.

The system and method of the present disclosure significantly improves detection of friction ridge details, namely those that have developed poorly or are considered borderline prints. FIG. 5 illustrates that fingerprints which were undetectable using conventional imaging techniques may be detected using chemical imaging. FIG. 5A is illustrative of a digital image of a sample. FIG. 5B is illustrative of a chemical image of a sample at 590 nm after flat field correction. FIG. 5C is illustrative of a chemical image of a sample at 590 nm after additional processing steps: reconstruction of PCA frames and noise reduction filtering. As can be seen from FIGS. 5A, 5B, and 5C, chemical imaging holds potential for increasing visualization of ninhydrin treated fingerprints on newspaper.

FIG. 6 illustrates the potential of the present disclosure for visualization of untreated prints on paper as well as successful background subtraction of multiple colors. FIG. 6A is illustrative of a digital image of a sample. FIG. 6B is illustrative of a chemical image of a sample at 430 nm after flat field correction. FIG. 6C is illustrative of a chemical image of a sample after additional processing steps: normalization, PCA, reconstruction, and concatenation. As can be seen from FIGS. 6A, 6B, and 6C, chemical imaging holds potential for increasing visualization of latent fingerprints on untreated white paper.

The system and method of the present disclosure hold potential for executing automated imaging of latent prints on documents while preserving the parent-child relationship between the original document and its enhanced latent prints. In one embodiment, system's throughput can be increased dramatically by the addition of two or more parallel developing and HSI stations.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the embodiments of the disclosure, it is noted that other variations and modifications will be apparent to those skilled in the art, and may be made without departing from the spirit of the disclosure.

What is claimed is:

1. A method comprising the steps of:
    (a) providing a sample document;
    (b) obtaining a digital image of said sample document;
    (c) treating said sample document with ninhydrin;
    (d) illuminating said sample document to thereby produce a first plurality of interacted photons wherein said first plurality of interacted photons are selected from the group consisting of: photons scattered by said sample document, photons reflected by said sample document, photons absorbed by said sample document, photons emitted by said sample document, and combinations thereof;
    assessing said first plurality of interacted photons to thereby generate a hyperspectral image representative of said sample document;
    (e) analyzing said hyperspectral image to thereby identify at least one region of interest of said sample document; and
    (f) obtaining a hyperspectral image of at least one of said regions of interest, wherein steps (b)-(d) are automated using robotics.

2. The method of claim 1 wherein said hyperspectral image comprises an image and a fully resolved spectrum unique to the material for each pixel location in said image.

3. The method of claim 2 wherein said hyperspectral image comprises a visible hyperspectral image.

4. The method of claim 1 wherein said digital image comprises a color digital image.

5. The method of claim 1 further comprising passing said first plurality of interacted photons through a tunable filter wherein said filter is selected from the group consisting of: a multi-conjugate tunable filter, a liquid crystal tunable filter, acousto-optical tunable filters, Lyot liquid crystal tunable filter, Evans Split-Element liquid crystal tunable filter, Solc liquid crystal tunable filter, Ferroelectric liquid crystal tunable filter, Fabry Perot liquid crystal tunable filter, and combinations thereof.

6. The method of claim 1 wherein said reagent comprises ninhydrin.

7. The method of claim 1 further comprising assigning an identifying mark to at least one of said digital image, said hyperspectral image representative of said sample document, said hyperspectral image representative of said region of interest, and combinations thereof.

8. The method of claim 7 wherein said identifying mark comprises a barcode.

9. The method of claim 1 further comprising analyzing said hyperspectral image representative of said region of interest to thereby determine at least one of: the presence of at least a portion of a fingerprint and the absence of at least a portion of a fingerprint.

10. The method of claim 1 wherein said region of interest of said document comprises an area of said document exhibiting high color contrast with respect to the rest of the document in response to said reagent.

11. The method of claim 1 wherein said region of interest comprises at least a portion of at least one latent fingerprint.

12. The method of claim 1 further comprising comparing at least one of a detected fingerprint, a portion of a detected fingerprint, and combinations thereof, to a reference data base comprising at least one reference fingerprint.

13. The method of claim 12 wherein each reference fingerprint in said reference data base is associated with a known individual.

14. The method of claim 13 wherein if said comparison results in a match, correlating the detected fingerprint with the individual associated with the reference fingerprint.

15. A system comprising:
    a first imaging station for obtaining a digital image representative of a sample document;
    a first processing station for treating said document with ninhydrin to thereby produce a treated document;
    a second processing station for developing said treated document;
    a second, imaging station for obtaining a hyperspectral image representative of at least one of: said document, a region of interest of said document, and combinations thereof; and
    a robotic subsystem for transporting said document through said system.

16. The system of claim 15 further comprising a means for mounting a sample document under analysis.

17. The system of claim 15 wherein said first imaging station and said second imaging station are the same.

18. The system of claim 15 wherein said first imaging station comprises:
    an illumination source for illuminating said document to thereby generate a first plurality of interacted photons;
    a collection optics for collecting said first plurality of interacted photons; and
    a detector for detecting said first plurality of interacted photons and generating a digital image representative of said document.

19. The system of claim 18 wherein said illumination source comprises a broadband white light source.

20. The system of claim 15 wherein said second imaging station comprises:
    an illumination source for illuminating at least one of said document and a region of interest to thereby generate a second plurality of interacted photons;
    a collection optics for collecting said second plurality of interacted photons;
    a tunable filter through which said second plurality of interacted photons are passed;
    a detector for detecting said second plurality of interacted photons to thereby generate a hyperspectral image representative of at least one of: said document, said region of interest of said document, and combinations thereof.

21. The system of claim 20 wherein said collection optics comprises a zoon lens.

22. The system of claim 20 wherein said tunable filter is selected from the group consisting of: a multi-conjugate tunable filter, a liquid crystal tunable filter, acousto-optical tunable filters, Lyot liquid crystal tunable filter, Evans Split-Element liquid crystal tunable filter, Solc liquid crystal tunable filter, Ferroelectric liquid crystal tunable filter, Fabry Perot liquid crystal tunable filter, and combinations thereof.

23. The system of claim 20 wherein said illumination source comprises a broadband white light source.

24. The system of claim 15 further comprising a computer control system for controlling the operation of said system.

25. The system of claim 15 further comprising a at least one image data base wherein said image data base comprises at least one of: a digital image representative of said document, a hypserpsectral image representative of said document, a hyperspectral image representative of a region of interest of said document, and combinations thereof.

26. The system of claim 15 further comprising a means for associating two or more of said digital image representative of said document, said hyperspectral image representative of said document, and said hyperspectral image representative of said region of interest of said document.

27. The system of claim 15 wherein environmental conditions present in said second processing station are controlled to thereby accelerate development of said document.

28. The system of claim 15 further comprising a reference data base comprising at least one reference fingerprint wherein said reference fingerprint is associated with a known individual.

29. The system of claim 28 further comprising a means for comparing a detected fingerprint on said sample document with said at least one reference fingerprint.

* * * * *